United States Patent
King et al.

(10) Patent No.: US 10,349,676 B2
(45) Date of Patent: Jul. 16, 2019

(54) VAPORIZATION AND DOSAGE CONTROL BY DIAPHRAGM PUMP FOR ELECTRONIC VAPORIZING INHALER

(71) Applicant: CTC Technologies, LLC, Chicago, IL (US)

(72) Inventors: Charles William King, Chicago, IL (US); Charles Dominic Corry, Chicago, IL (US); Christopher Mingilino, Chicago, IL (US); Timothy Tutt, Chicago, IL (US); Thomas Fornarelli, Chicago, IL (US)

(73) Assignee: AVANZATO TECHNOLOGY CORP., Chicago, IL (US)

( * ) Notice: Subject to any disclaimer, the term of this patent is extended or adjusted under 35 U.S.C. 154(b) by 0 days.

(21) Appl. No.: 15/038,455

(22) PCT Filed: Nov. 21, 2014

(86) PCT No.: PCT/US2014/066949
§ 371 (c)(1),
(2) Date: May 21, 2016

(87) PCT Pub. No.: WO2015/077645
PCT Pub. Date: May 28, 2015

(65) Prior Publication Data
US 2016/0286865 A1 Oct. 6, 2016

Related U.S. Application Data

(60) Provisional application No. 62/067,762, filed on Oct. 23, 2014, provisional application No. 61/906,928, filed on Nov. 21, 2013.

(51) Int. Cl.
*A24F 47/00* (2006.01)
*A61M 11/00* (2006.01)
(Continued)

(52) U.S. Cl.
CPC ......... *A24F 47/008* (2013.01); *A61M 11/005* (2013.01); *A61M 11/042* (2014.02);
(Continued)

(58) Field of Classification Search
CPC .. A61M 11/042; A61M 11/005; A61M 15/06; A61M 2016/0021;
(Continued)

(56) References Cited

U.S. PATENT DOCUMENTS 5,894,841 A 4/1999 Voges
7,832,410 B2 11/2010 Hon
(Continued)

FOREIGN PATENT DOCUMENTS

EP 2273933 1/2011
EP 2468118 6/2012
(Continued)

OTHER PUBLICATIONS

Written Opinion of the ISA, dated Apr. 15, 2015, for PCT/US2014/066949.
(Continued)

*Primary Examiner* — Harshad C Patel
(74) *Attorney, Agent, or Firm* — Flener IP & Business Law; Zareefa B. Flener

(57) ABSTRACT

The present invention provides an electronic vaporizing inhaler with an electrical storage device; a liquid reservoir for vaping liquid; a vaporizer with a substrate defined by a plurality of capillary apertures that provide fluid communication between the vaporizer and the liquid reservoir; a sponge; a wick; and a heating element; a microprocessor in electrical communication with the electrical storage device that directs current from the electrical storage device to the heating element in the vaporizer; a sensor configured to detect when a user draws on the electronic cigarette that
(Continued)

activates the microprocessor when it detects that a user has drawn on the electronic cigarette; a housing having designed to contain the electrical storage device, vaporizer, microprocessor, sensor, and liquid reservoir and having a mouthpiece from which a user can inhale vapor from the vaporizer. The invention also provides a dosage control embodiment using a heat or diaphragm pump.

10 Claims, 10 Drawing Sheets

(51) Int. Cl.
| | |
|---|---|
| A61M 15/06 | (2006.01) |
| A61M 11/04 | (2006.01) |
| F22B 1/28 | (2006.01) |
| H02J 7/00 | (2006.01) |
| H02J 7/02 | (2016.01) |
| H05B 1/02 | (2006.01) |
| A61M 16/00 | (2006.01) |

(52) U.S. Cl.
CPC ............ *A61M 15/06* (2013.01); *F22B 1/284* (2013.01); *H02J 7/0052* (2013.01); *H02J 7/025* (2013.01); *H05B 1/0297* (2013.01); *A61M 2016/0021* (2013.01); *A61M 2016/0027* (2013.01); *A61M 2205/50* (2013.01)

(58) Field of Classification Search
CPC ....... A61M 2016/0027; A61M 2205/50; F22B 1/284; H05B 1/0297
USPC .......................................... 131/329
See application file for complete search history.

(56) References Cited

U.S. PATENT DOCUMENTS

| | | | | |
|---|---|---|---|---|
| 2007/0267031 | A1* | 11/2007 | Hon | ............... A24F 47/008 131/273 |
| 2010/0200008 | A1* | 8/2010 | Taieb | ............... A24F 47/008 131/360 |
| 2011/0011396 | A1* | 1/2011 | Fang | ............... A24F 47/008 128/202.21 |
| 2013/0213418 | A1 | 8/2013 | Tucker et al. | |
| 2013/0220315 | A1 | 8/2013 | Conley et al. | |
| 2013/0284192 | A1 | 10/2013 | Peleg | |
| 2013/0284194 | A1 | 10/2013 | Newton | |
| 2014/0196734 | A1* | 7/2014 | Liu | ............... A24F 47/008 131/329 |
| 2015/0173419 | A1* | 6/2015 | Tu | ............... A24F 47/008 131/329 |
| 2016/0128385 | A1* | 5/2016 | Lin | ............... A24F 47/002 131/328 |
| 2016/0286860 | A1* | 10/2016 | Flayler | ............... A24F 47/008 |

FOREIGN PATENT DOCUMENTS

| | | |
|---|---|---|
| EP | 2468118 A1 | 6/2012 |
| WO | 2012072762 A1 | 6/2012 |
| WO | WO2012072762 | 6/2012 |
| WO | 2012152053 A1 | 11/2012 |
| WO | 2013083634 A1 | 6/2013 |

OTHER PUBLICATIONS

European Search Report, dated Sep. 13, 2017, for EP 14 86 4730.
Extended European search report for PCT/US2014066949, published Mar. 6, 2018.

* cited by examiner

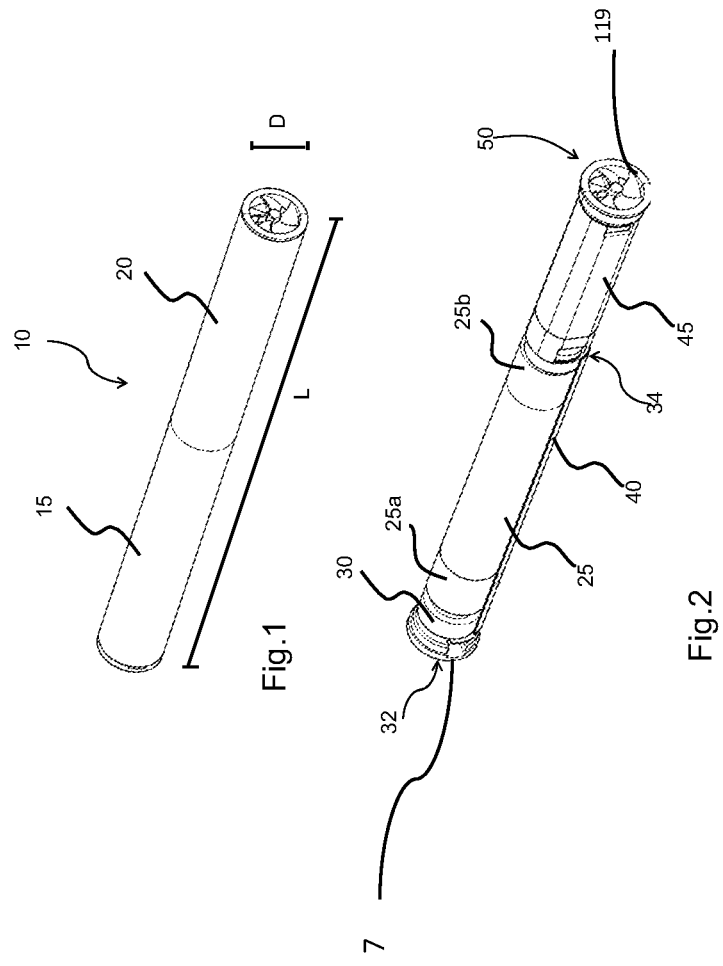

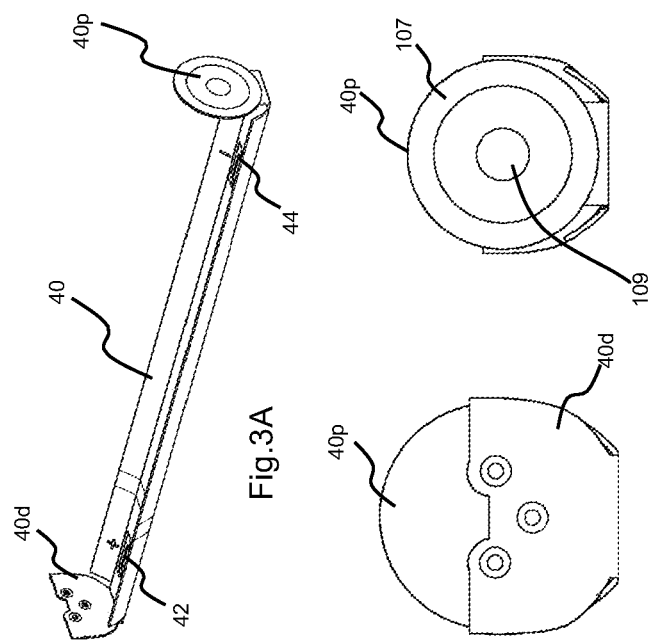

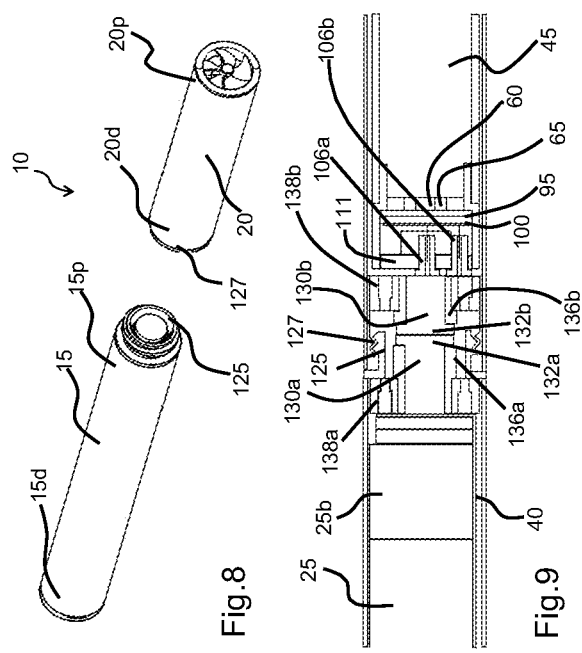
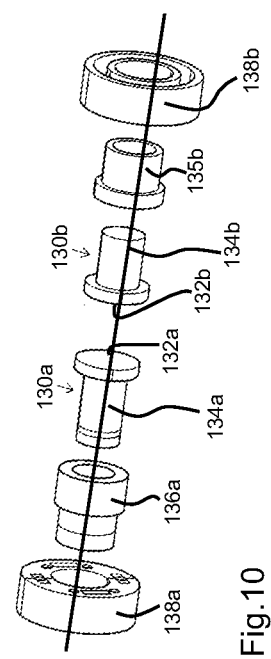
Fig. 8
Fig. 9
Fig. 10

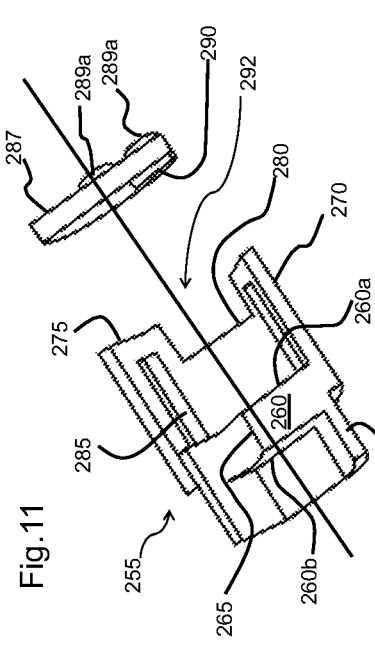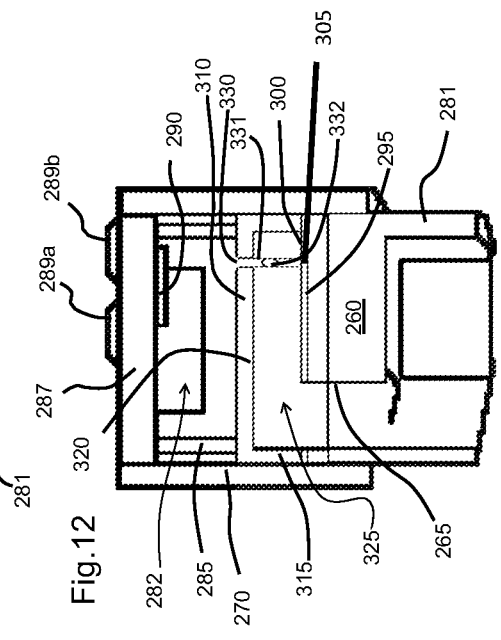

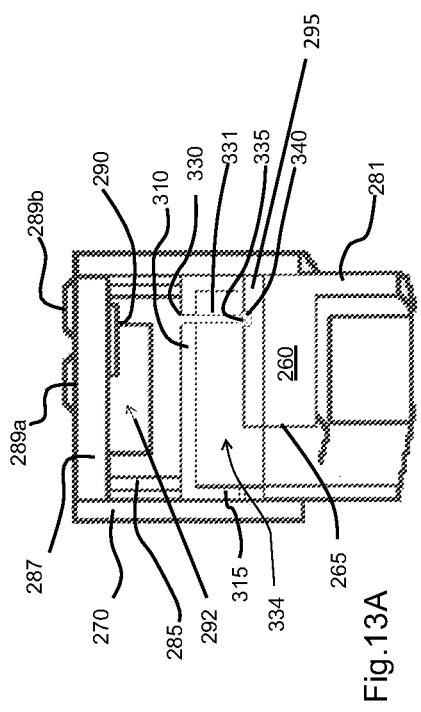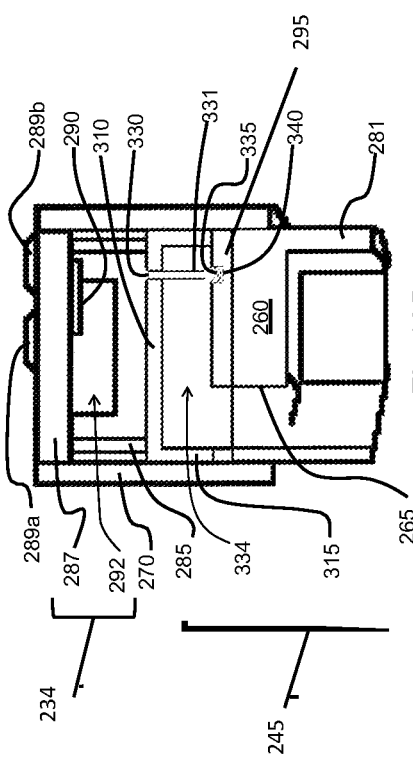

VAPORIZATION AND DOSAGE CONTROL BY DIAPHRAGM PUMP FOR ELECTRONIC VAPORIZING INHALER

CROSS-REFERENCE TO RELATED APPLICATIONS

This application claims the benefit of priority to U.S. Provisional Patent Application No. 61/906,928, filed on Nov. 21, 2013, and to U.S. Provisional Patent Application No. 62/067,762, filed on Oct. 23, 2014.

BACKGROUND OF THE INVENTION

1. Field of the Invention

This invention is directed to an electronic cigarette that provides consistent dosage and that is better able to withstand drops and other mechanical shocks during assembly and use.

2. Background of the Invention

Electronic cigarettes are becoming popular among smokers who wish to satisfy a nicotine craving but who also want to avoid the tar and other harsh chemicals associated with traditional cigarettes. Electronic cigarettes contain liquid nicotine, which is typically a mixture of nicotine oil, a solvent (such as propylene glycol, vegetable glycerin, or a combination of both), water, and sometimes flavoring. When the user draws, or inhales, on the electronic cigarette, the liquid nicotine is drawn into a vaporizer where it is heated into a vapor. As the user draws on the electronic cigarette, he or she inhales the vapor containing the nicotine.

Electronic cigarettes and other vapor inhalers typically have similar designs. Most feature a liquid nicotine reservoir with an interior membrane, such as a sponge, fabric wadding (typically cotton), or other fibrous material, that holds the liquid nicotine so as to prevent leaking from the reservoir. Nevertheless, these cigarettes are still prone to leaking because there is no impediment to prevent the liquid from flowing out of the membrane and into the mouthpiece. A leaking electronic cigarette is problematic for several reasons. First, the liquid can leak into the electronic componentry, which can cause impaired performance of the device. Second, leaks waste the liquid nicotine mixture. Finally, the liquid can leak into the electronic cigarette mouthpiece, and the user may inhale the unvaporized liquid, which provides an unsatisfying vaping experience.

Electronic cigarettes are also known to provide inconsistent doses between draws. The aforementioned leaking is one cause of inconsistent doses because the membrane may be oversaturated or undersaturated near the vaporizer. If the membrane is oversaturated, then the user may experience a stronger than desired dose of vapor, and if the membrane is undersaturated, then the user may experience a weaker than desired dose of vapor. Additionally, small changes in the strength of the user's draw may provide stronger or weaker doses. Inconsistent dosing, along with leaking, can lead to faster consumption of the vaping liquid.

Additionally, conventional electronic cigarettes are often unreliable in that the electronic components fail when the electronic cigarette is dropped or subjected to other mechanical shock. Conventional electronic cigarettes have multiple wires that run between various components and that are held in electrical communication with solder joints. The solder joints are prone to break, which can prevent the electronic cigarette from functioning to its full capacity if any function is even possible. Typically, electronic cigarettes are assembled by hand which increases the possibility for poor soldering. Moreover, when the electronic cigarette is assembled, the wires are stuffed into the housing in any way that they will fit. This can cause stress on the solder joints, leading to breaks.

Conventional electronic cigarettes also predominantly use nichrome heating elements. Nichrome is an alloy primarily consisting nickel and chromium, and it is used in many electric heater applications. However, nichrome can reach temperatures as high as 900° C. very quickly, which presents several issues for a consumer product. First, some of the chromium may leach out of the heating element and be inhaled by the user. Second, the high temperature of the heating element is dangerous to the user. Third, the heating element can burn the vaping fluid, which not only causes a poor taste but also can degrade certain chemicals in the vaping liquid. Finally, by operating at such a high temperature, the electronic cigarette will consume more energy, resulting in shorter battery life.

Thus a need exists in the art for an electronic cigarette that is better able to withstand leaks and occasional drops or other mishandling and that provides consistent dosing.

SUMMARY OF THE INVENTION

An object of the present invention is to improve upon the deficiencies of conventional electronic cigarettes and other electronic vaporizing inhalers.

Another object of the present invention is to provide an electronic vaporizing inhaler that has improved resistance to leaks. A feature of the present invention is that the liquid to be vaporized is distributed through a series of capillaries that are able to contain the vaping liquid based on the surface tension of the liquid and that allows flow of the vaping liquid in response to small changes in pressure. An advantage of the present invention is that the liquid to be vaporized only flows through the capillary when the user draws on the electronic cigarette.

Another object of the present invention is to provide an electronic vaporizing inhaler in which the dose of vaporized liquid is consistent. A feature of the present invention is that the liquid reservoir dispenses the vaping liquid using capillary action. An additional feature of the present invention is that the microprocessor has a timer that shuts off the heating element after a preprogrammed time in order to avoid a large dose of vaping liquid. An advantage of the present invention is that the user receives a consistent dose of vaporized liquid with each and every draw.

A further object of the present invention is to provide an electronic vaporizing inhaler with reliable parts. A feature of the present invention is that the components of the cigarette are joined using solder-less connections and electrical communication between components is made using foils instead of wires. An advantage of the present invention is that the electronic cigarette is better able to withstand drops and other accidents.

Yet another object of the present invention is to provide an electronic vaporizing inhaler that has customizable dosing. A feature of one embodiment of the present invention is that customizable doses can be provided using a microprocessor that controls a heat pump. A feature of another embodiment of the present invention is that customizable doses are delivered using a microprocessor that controls a diaphragm pump. An advantage of the present invention is that the user can select the user can adjust the dose of vaping liquid delivered in a single puff or over the course of a day.

The present invention provides An electronic vaporizing inhaler, said electronic vaporizing inhaler comprising: an electrical storage device; a liquid reservoir adapted to receive vaping liquid; a vaporizer, comprising: a substrate defined by a plurality of capillary apertures, wherein the capillary apertures provide fluid communication between the vaporizer and the liquid reservoir; a sponge in physical contact with the substrate; a wick in physical contact with the sponge; and a heating element proximal to the wick; a microprocessor in electrical communication with the electrical storage device, wherein the microprocessor is configured to direct current from the electrical storage device to the heating element in the vaporizer; a sensor configured to detect when a user draws on the electronic cigarette, wherein the sensor is in electrical communication with the microprocessor and wherein the sensor activates the microprocessor when it detects that a user has drawn on the electronic cigarette; a housing having a first end and a second end, wherein the housing is designed to contain the electrical storage device, vaporizer, microprocessor, sensor, and liquid reservoir and wherein the second end of the housing is a mouthpiece from which a user can inhale vapor from the vaporizer.

The present invention also provides an electronic vaporizing inhaler, said electronic vaporizing inhaler comprising: an electrical storage device; a liquid reservoir adapted to receive vaping liquid; a vaporizer, comprising: a heating chamber, comprising: a substrate having a plurality of apertures, wherein the plurality of apertures provide fluid communication between the vaporizer and the liquid reservoir; a first heating element, wherein the first heating element heats the vaping liquid to a temperature sufficient to create and burst a vapor bubble; a superior end having a plurality of nozzles, wherein the nozzle ejects the vaping liquid when the vapor bubble bursts; a second heating element proximal to the nozzle; a microprocessor in electrical communication with the electrical storage device, wherein the microprocessor is configured to direct current from the electrical storage device to the first and second heating elements in the vaporizer; a sensor configured to detect when a user draws on the electronic cigarette, wherein the sensor is in electrical communication with the microprocessor and wherein the sensor activates the microprocessor when it detects that a user has drawn on the electronic cigarette; a housing having a first end and a second end, wherein the housing is designed to contain the electrical storage device, vaporizer, microprocessor, sensor, and liquid reservoir and wherein the second end of the housing is a mouthpiece from which a user can inhale vapor from the vaporizer.

Additionally, the present invention provides an electronic vaporizing inhaler, said electronic vaporizing inhaler comprising: an electrical storage device; a liquid reservoir adapted to receive vaping liquid; a vaporizer, comprising: a primer chamber, comprising: an inferior end having a plurality of apertures, wherein the plurality of apertures provide fluid communication between the vaporizer and the liquid reservoir; a substrate embedded with a plurality of diaphragm pumps, each diaphragm pump comprising a diaphragm and a piezoelectric transducer, wherein the each diaphragm flexes inwardly and outwardly in response to its corresponding piezoelectric transducer; and a superior end having a plurality of nozzles, wherein each nozzle ejects the vaping liquid when its corresponding diaphragm flexes inwardly; a heating element proximal to the nozzle; a microprocessor in electrical communication with the electrical storage device, wherein the microprocessor is configured to direct current from the electrical storage device to the heating element in the vaporizer and to the piezoelectric transducer; a sensor configured to detect when a user draws on the electronic cigarette, wherein the sensor is in electrical communication with the microprocessor and wherein the sensor activates the microprocessor when it detects that a user has drawn on the electronic cigarette; a housing having a first end and a second end, wherein the housing is designed to contain the electrical storage device, vaporizer, microprocessor, sensor, and liquid reservoir and wherein the second end of the housing is a mouthpiece from which a user can inhale vapor from the vaporizer.

BRIEF DESCRIPTION OF THE DRAWINGS

The invention together with the above and other objects and advantages will be best understood from the following detailed description of the preferred embodiment of the invention shown in the accompanying drawings, wherein:

FIG. 1 is a perspective view of an electronic cigarette embodiment of the present invention;

FIG. 2 is a perspective view of the components of the electronic cigarette embodiment absent the housing;

FIGS. 3A-C depict various views of the flexible circuit;

FIG. 8 depicts a reusable embodiment of the presently invented electronic cigarette;

FIG. 9 depicts a sectional view of the reversible joint of the reusable embodiment;

FIG. 10 depicts an exploded view of the components providing electrical communication between the two portions of the reusable embodiment;

FIG. 11 depicts the cap region of the dosage control embodiment;

FIG. 12 depicts the heat pump variety of the dosage control embodiment;

FIG. 13A-B depicts the diaphragm pump variety of the dosage control embodiment;

DETAILED DESCRIPTION OF THE INVENTION

Figure 4:
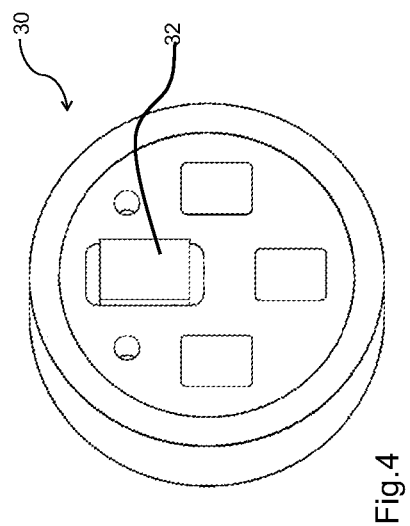
FIG. 4 depicts the microprocessor of the invented electronic cigarette.

The foregoing summary, as well as the following detailed description of certain embodiments of the present invention, will be better understood when read in conjunction with the appended drawings.

As used herein, an element recited in the singular and preceded with the word "a" or "an" should be understood as not excluding plural of said elements, unless such exclusion is explicitly stated. Furthermore, the references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention is directed to an electronic vaporizing inhaler. One specific embodiment of the electronic vaporizing inhaler is an electronic cigarette. The description of the invention and accompanying figures will be directed to the electronic cigarette embodiment; however, other embodiments are envisioned, such as a vaporizer for hookah, flavored liquids, medicine, and herbal supplements. Additionally, the device can be packaged to look like an object other than a cigarette. For instance, the device could resemble another smoking instrument, such as a pipe, water pipe, or slide, or the device could resemble another non-smoking related object.

Mesh Membrane Embodiment

Electronic cigarettes are either disposable or reusable. The term "reusable" as used herein implies that the energy storage device is rechargeable or replaceable or that the vaping liquid is able to be replenished either through refilling or through replacement of the vaping liquid cartridge. Alternatively, in some embodiments reusable electronic device is both rechargeable and the liquid can be replenished. A disposable embodiment will be described first, followed by a description of a reusable embodiment.

FIG. 1 depicts a disposable electronic cigarette embodiment 10 of the invented electronic vaporizing inhaler. As can be seen in FIG. 1, the electronic cigarette 10 has a cylindrical body with a relatively long length "L" as compared to the diameter "D." In terms of shape and appearance, the electronic cigarette 10 is designed to mimic the look of a typical cigarette. For instance, the electronic cigarette can feature a first portion 15 that primarily simulates the tobacco rod portion of a cigarette and a second portion 20 that primarily simulates a filter. In the disposable embodiment of the invented device, the first portion and second portion are regions of a single, non-separable device. The designation of a first portion and a second portion is used to conveniently differentiate the components that are primarily contained in each portion.

As can be seen in FIG. 2, the first portion 15 contains the power and control components. An electrical storage device 25 powers the electronic cigarette 10. The electrical storage device 25 can be a battery, including but not limited to a lithium-ion, alkaline, zinc-carbon, nickel-metal hydride, or nickel-cadmium battery; a super capacitor; or a combination thereof. In the disposable embodiment, the electrical storage device 25 is not rechargeable, but, in the reusable embodiment, the electrical storage device 25 would be selected for its ability to recharge. In the disposable embodiment, the electrical storage device 25 is primarily selected to deliver a constant voltage over the life of the device. Otherwise, the performance of the electronic cigarette would degrade over time. Preferred electrical storage devices that are able to provide a consistent voltage output over the life of the device include lithium-ion and lithium polymer batteries.

The electrical storage device 25 is in electrical communication with a flexible circuit board 40. Electrical communication between the various components of the electronic cigarette 10 is preferably made using a flexible circuit boards 40 or through direct electrical contact. Using flexible circuits 40 instead of soldered wire connections improves the reliability of the device. Soldered connections are known to break when the device containing them is subject to mechanical shock, such as from a drop. When the soldered connection breaks, operation of the device will be impaired if it operates at all. Flexible circuits 40 provide reliable connections that are better able to withstand mechanical shocks, and the flexible circuits 40 are able to provide a more compact design.

The manufacturing of the embodiment 10 is also easier using the flexible circuit 40 as compared with soldering individual wires which require manual manipulation and several soldering tasks.

The electrical storage device 25 has a first end 25a that generally corresponds to a positive terminal and a second end 25b that generally corresponds to a negative terminal. As can be seen in FIG. 3A, the flexible circuit board 40 has a proximal end 40p and a distal end 40d. The positive terminal at the first end 25a of the electrical storage device 25 is in electrical communication with a positive lead 42 near the distal end 40d of the flexible circuit board 40. The negative terminal at the second end 25b of the electrical storage device 25 is in electrical communication with a negative lead 44 near the proximal end 40p of the flexible circuit board 40. The distal end 40d of the flexible circuit board 40 is in electrical communication with a microprocessor 30. As shown in FIG. 4, the microprocessor 30 is a commercially available unit that has a sensor and LED light 32 incorporated into its design; however, the sensor and light 32 can be separate components. The microprocessor 30 is configured to process data from the pressure sensor, to control the light 32 (if included) on the first portion 15, to direct current flow to a vaporizer 34 in the second portion 20, and to terminate current flow after a preprogrammed amount of time.

Figure 15:
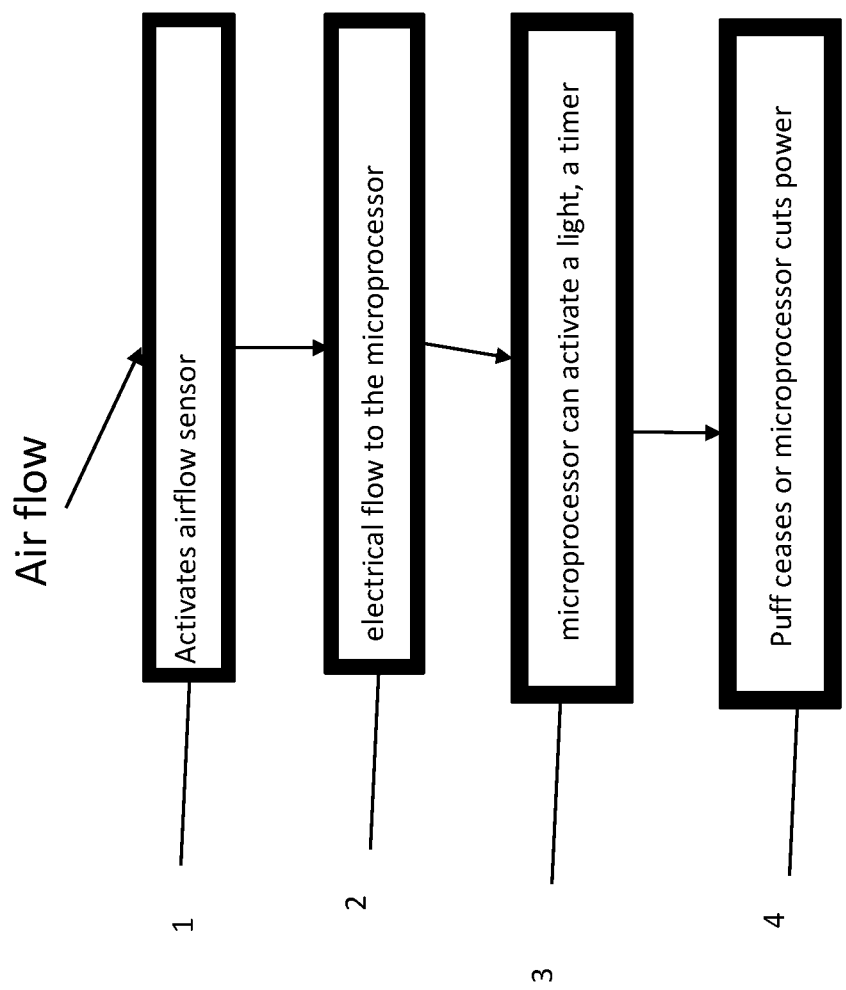
FIG. 15 depicts a flow chart of how the sensor operates to activate and deactivate the microprocessor.

As shown in FIG. 15, step 1 illustrates the sensor 32 detecting when the electronic cigarette 10 is in use (i.e., when the user draws on the embodiment) and, in response, activates the microprocessor 30. The sensor can be selected to detect changes in pressure, air flow, or vibration. In a preferred embodiment, the sensor is a mechanical pressure sensor. In this embodiment, the pressure sensor is a switch that allows current flow to the microprocessor in response to a change in pressure when the user draws on the electronic cigarette 10 (step 2) and air flows through the air flow apertures 7. In another preferred embodiment, the sensor is a digital pressure sensor such that gradations of pressure can be sensed (step 1). In this embodiment, the digital pressure sensor would pulse off and on to measure any change in pressure. In the digital embodiment, the sensor takes continuous readings which in turn requires the digital sensor to continuously draw current, but the amount is small and overall battery life would be negligibly affected. The digital sensor allows for a direct measurement of the change in the pressure (step 1).

In embodiments featuring a light 32, the microprocessor 30 is in electrical communication with the light 32. The light 32 serves as an indicator that the electronic cigarette 10 is in use, i.e., the light will glow when the user inhales (step 3). The intensity of the glow can be tailored to the strength of the user's inhale, meaning that a relatively stronger inhale will cause the light 32 to glow brighter, while a relatively weaker inhale will cause the light to glow dimmer. The color of light emitted from the light 32 can be any color. For instance, the color could be orange or red to simulate the glowing ember of a burning cigarette. In other instances, the color is selected specifically to avoid the appearance of a traditional cigarette so as to assuage the concerns of onlookers about harmful secondhand smoke.

Additionally, the microprocessor 30 includes a timer. Once the microprocessor 30 is activated by the sensor, the timer initiates (step 3). In one embodiment, the airflow cessation causes the sensor to disconnect the circuit thus shorting the power to the sensor and stopping the vaping process (step 4). In another embodiment, the timer will stop after a certain amount of preprogrammed time (step 4). After a preprogrammed amount of time, the timer will shut off the microprocessor 30, which terminates current flow to the vaporizer 34. In this way, the dose of vaping liquid is consistent between draws and limited. In a preferred embodiment, the timer will deactivate the microprocessor after five seconds; however, longer or shorter times could also be used. Because the microprocessor 30 operates on a timer, the microprocessor 30 eliminates the requirement to regulate the temperature of the vaporizer 34 which also eliminates the need to measure the temperature of the vaporizer 34.

Returning to FIG. 2, the second portion 20 of the electronic cigarette 10 is generally comprised of a vaporizer 34, a liquid reservoir 45, and a mouthpiece 50.

Figure 5:
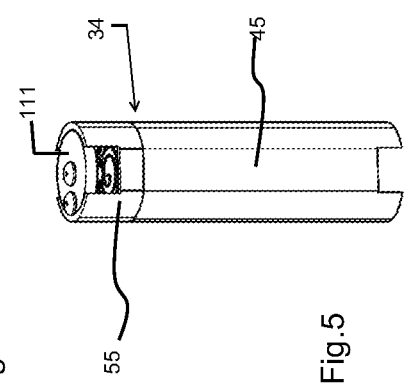
FIG. 5 depicts the vaporizer and liquid reservoir of the invented electronic cigarette.

In the embodiment shown in FIG. 5, the vaporizer 34 and liquid reservoir 45 are part of a single cartridge wherein the vaporizer 34 is incorporated in a cap 55 for the liquid reservoir 45.

Figure 6:
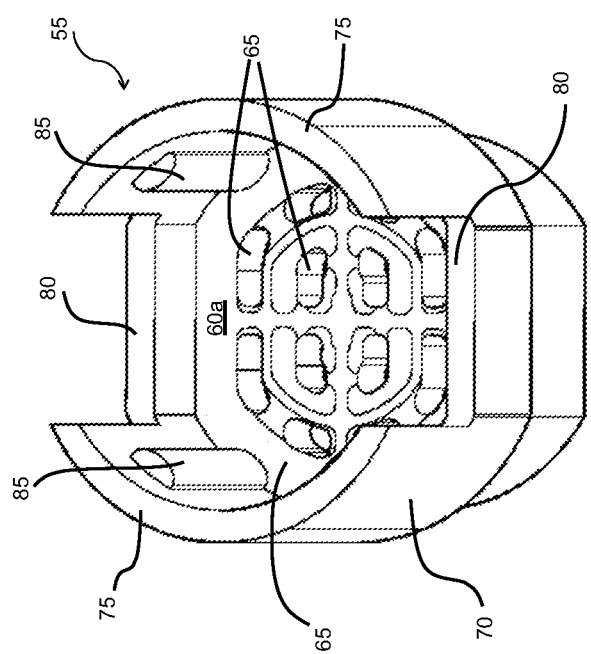
FIG. 6 depicts a perspective view of the reservoir cap.
Figure 7:
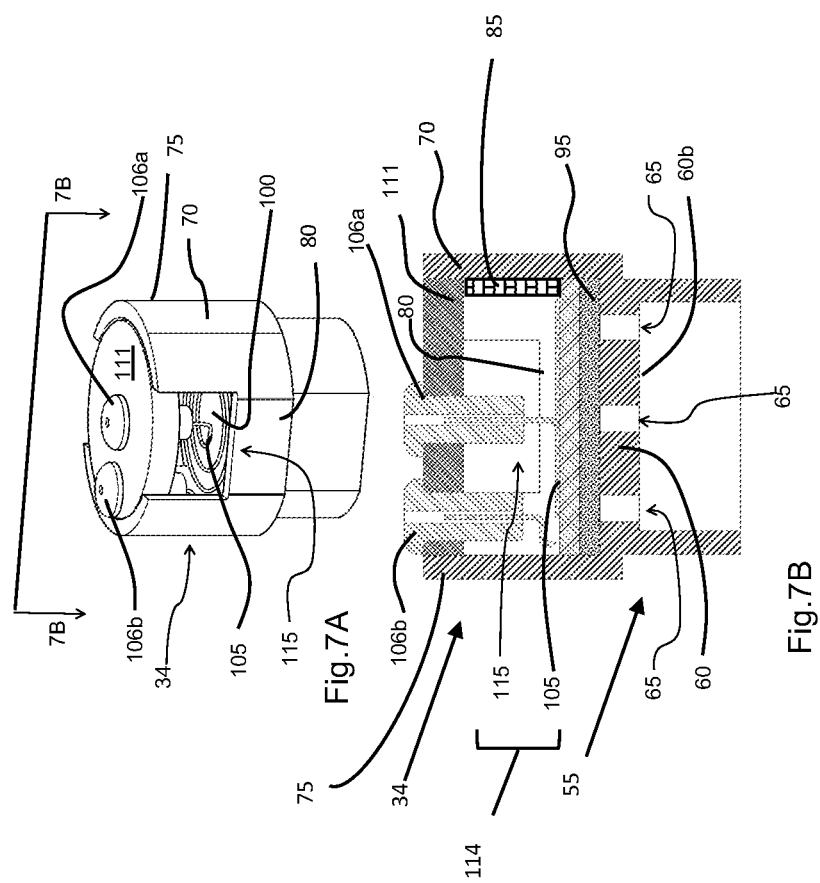
FIG. 7A depicts a perspective view of the vaporizer of the invented electronic cigarette.
FIG. 7B depicts a sectional view of the vaporizer depicted in FIG. 7A taken along line 7B-7B.

As shown in FIG. 6, the cap 55 is comprised of an intermediate partition 60, having a first surface 60a and a second surface 60b (shown in FIG. 7B). The intermediate partition 60 defines a plurality of transversely extending apertures 65. The apertures 65 create capillaries from the second surface 60b through the thickness of the intermediate partition 60 to the first surface 60a. The apertures 65 can vary in diameter from approximately 1 mm to approximately 4 mm (the diameter of the capillary aperture will be dictated to a large extent by the viscosity of the fluid—a more viscous fluid can have a larger diameter capillary without leaking, while a less viscous fluid will require a smaller diameter capillary). In an embodiment of the present invention, the partition 60 is 1 mm thick and has a first outer ring of apertures 65 that are 1.3 mm wide and a central aperture 65 that is 1.5 mm wide.

Generally speaking, the diameters of the capillaries are sufficient to facilitate passage of the not yet vaporized fluid. Suitable viscosities of the fluid are below approximately 100 centipoises (cP), preferably between 30 and 90 cP and most preferably between 45 and 75 cP. An embodiment of the invention utilizes a viscosity of approximately 60 cP.

A myriad of means exists to maintain the viscosity of the vaping liquid at the desired below 100 cP point. Inasmuch as the mixture is volatilized at relatively low temperatures compared to the light off temperatures of state of the art e-cigarette configurations, vapor pressures of the mixture should be kept to a minimum. As such, thinning agents, having both polar and nonpolar qualities are suitable, and such agents include alcohols, carboxylic acids, and similar water miscible compounds containing hydroxyl, carboxyl or carbonyl moieties.

In an embodiment of the invention, ethanol is utilized to maintain the viscosity of the mixture at about 60 cP. The mixture fluid is preheated to approximately 60° C. and diluted approximately 10 to 60 percent with ethanol, preferably between approximately 15 and 30 percent, ethanol and most preferably about 15-18 percent ethanol. In an embodiment of the invention, 17 percent ethanol dilution was utilized.

The apertures 65 can be circular or any other of a variety of geometric shapes. As depicted in FIG. 6, the apertures 65 are elliptical or bent ellipses. The fluid passageway provided by the aperture establishes fluid communication between the liquid reservoir 45 and the cap 55.

Extending from the first surface 60a of the partition 60 is a perimeter wall 70. The perimeter wall 70 has tall regions 75 and short regions 80. In the tall regions 75, the height of the perimeter wall 70 is higher than the height of the short regions 80. Protruding from the medially facing surface of the tall regions 75 of the perimeter wall 70 is a plurality of ridges 85.

Extending from the second surface 60b of the partition 60 is a plug 90. The plug 90 is defined by a ring wall that is indented from the periphery of the second surface 60b. The plug 90 is inserted into the liquid reservoir 45. Preferably, when the plug 90 is inserted in the liquid reservoir 45, the perimeter wall 70 forms a smooth and continuous surface with the exterior of the liquid reservoir 45.

The perimeter wall 70 and intermediate partition 60 define a cavity. As depicted in FIG. 7B, inserted into the cavity and in contact with the intermediate partition 60 is a sponge 95. The sponge 95 absorbs vaping liquid from the liquid reservoir 45 through the apertures 65. The sponge 95 is overlaid with a wick 100. The wick 100 transports vaping liquid to the vaporizer 34 via capillary action. Preferably the wick 100 is a fiberglass wick; however, cotton, paper, or other fiber strands could be used for a wick material. In one embodiment of the electronic cigarette, the liquid reservoir 45 contains a flexible bladder that maintains pressure on the vaping liquid in the liquid reservoir. This pressure is balanced against the surface tension of the liquid at the aperture 65 of the capillaries in the partition 60 such that a small change in pressure allows flow but the capillaries do not leak otherwise.

As can be seen in FIG. 7A, a heating element 105 is placed directly above the wick 100. As depicted in FIG. 7A, the heating element 105 is a coil, but other heating elements can also be used, such as thin films and thick films. In a preferred embodiment, the heating element has a positive temperature coefficient ("PTC"), i.e., the electrical resistance of the heating element 105 increases as the temperature increases. In this way, the maximum temperature of the heating element cannot exceed a material-specific amount because current flow will be cut off by the increased electrical resistance. Accordingly, the material used for the heating element 105 can be selected to ensure that the electronic cigarette 10 operates within a desired temperature range. A desirable temperature range for vaping liquid is typically between 100° C. and 300° C. at atmospheric pressure, and an even more desirable temperature range at which the heating element operates is between 150° C. and 250° C. at atmospheric pressure.

A variety of PTC materials can also be used for the heating element 105. Suitable heating elements for the coil heater include wire nickel-iron alloys on a mica former. Suitable heating elements for the thin film and thick film heaters could be constructed of a carrier of alumina, zirconium oxide, calcium oxide, silicon dioxide, potassium oxide, magnesium oxide, boron carbide, sodium oxide, and combinations thereof. In embodiment of the invention, alumina was the chosen carrier.

Conductor coatings are electrically conductive substrates comprised of metals, such as those selected from the group consisting of silver, palladium, gold, copper, aluminum, tungsten, zinc, or alloys thereof; films of nickel, platinum, molybdenum, iron, steel, and alloys thereof; a glaze, such as DuPont overglaze ink; and self-leveling printed epoxy covercoats. The thick film heaters differ from the thin film heaters in two respects: thickness and deposition technique.

The thick film heaters can be deposited in more ways, such as through printed resistive inks, while the thin films can be sputter coated on a substrate.

When the user draws on the electronic cigarette 10, the vaping liquid is drawn from the reservoir 45, through the plurality of apertures 65, and into the sponge 95 and wick 100. The wick 100 brings the vaping liquid into contact with the heating element 105 of the vaporizer 34. The user's draw also causes the sensor to activate the microprocessor 30, which directs current to the heating element 105. Thus, when the user draws on the mouthpiece 50 of the electronic cigarette 10, two actions happen simultaneously. First, the sensor activates the microprocessor 30, which triggers the heating element 105 to begin heating. Second, the draw reduces the pressure outside the reservoir 45 such that flow of the vaping liquid through the apertures 65 begins, which saturates the sponge 95. The wick 100 transports the vaping liquid to the heating element 105, which vaporizes the liquid. Typically, the heating element 105 will achieve a temperature of approximately 230° C. and the vaping liquid will be vaporized by the heating element 105 within 0.5 seconds of the user's first draw.

The heating element 105 is in electrical communication with electrical contacts 106a, 106b. Returning to FIG. 3C, the proximal end 40p of the flexible circuit board 40 has an outer electrode 107 and an inner electrode 109. The inner electrode 109 contacts the first electrical contact 106a, and the outer electrode 107 contacts the second electrical contact 106b. Via the flexible circuit board 40, the first electrical contact 106a is in electrical communication with the positive terminal of the electrical storage device 25 by way of the microprocessor 30, while the second electrical contact 106b is in electrical communication with the negative terminal of the electrical storage device 25.

The electrical contacts 106a, 106b are embedded in a disc 111. The disc 111 is designed to be received inside the perimeter wall 70 of the cap 55. The disc 111 rests on the ridges 85, thereby creating a vaporizing chamber 114. The disc 111 can be made using a variety of thermoplastic materials. Additionally, the disc 111 can be made of FR4, which is commonly used to make printed circuit boards.

Because the perimeter wall 70 is comprised of tall regions 75 and short regions 80, the combination of the cap 55 and disc 111 creates windows 115 in the perimeter wall 70. These windows 115 allow the vapor to escape from the vaporizer 34. The vapor flows out the windows 115, around the exterior of the liquid reservoir 45, and to the mouthpiece 50. In a preferred embodiment, the mouthpiece 50 is comprised of a diffuser (not shown) and a vortex outlet 119. The diffuser is a disc with a central aperture that concentrates the vapor into the vortex outlet 119. The combination of the diffuser and vortex outlet 119 control the pressure drop of the electronic cigarette 10 and prevent the whistling noise associated with the mouthpiece of some conventional electronic cigarettes.

Reusable Embodiment

Turning to the reusable embodiment depicted in FIG. 8, the first portion 15 and second portion 20 are separate components that can be reversibly joined together.

In the reusable embodiment, the components are substantially the same. The differences in the reusable embodiment vis-á-vis the disposable embodiment are the accommodations made to reversibly attach the first portion 15 and second portion 20 (often with reusable electronic cigarettes the second portion 20 is referred to as a "cartomizer" because it contains the liquid cartridge and vaporizer). The first portion 15 has a distal end 15d and a proximal end 15p, and the second portion 20 has a distal end 20d and a proximal end 20p. In the reusable embodiment, the first portion 15 and second portion 20 are reversibly attachable, such that the proximal end 15p of the first portion 15 is attached to the distal end 20d of the second portion 20. A variety of suitable connections can join the first portion 15 to the second portion 20, including magnetic joints, snap lock joints, and pin and groove joints, among others. In a preferred embodiment, which is described in the following, the first portion 15 and second portion 25 are joined using a threaded connection.

Because the electrical storage device 25 is located in the first portion 15 and the vaporizer 34 is located in the second portion 15, the joint needs to provide electrical communication between those components. In the present invention, electrical communication is established using electrodes that are compressed together when the first portion 15 is tightened into the second portion 20. As depicted in FIG. 8, the first portion 15 has a male threaded end 125 that is adapted to be received by a female threaded end 127 on the second portion 20. The male threaded end 125 and the female threaded end 127 have interior cavities that are adapted to receive the components that provide electrical communication between the first portion 15 and the second portion 20.

Electrical communication is established by compressing electrodes in the first portion 15 to electrodes in the second portion 20. As can be seen in FIG. 9, the first portion 15 contains a central pin electrode 130a, second portion 20 contains a central pin 130b. The central pins each have broad, flat heads 132a, 132b that contact each other. The shafts 134a of the central pin 130a of the first portion 15 contacts the inner electrode 109 on the proximal end 40p of the flexible circuit 40. The shaft 134b of the central pin 130b of the second portion 20 contacts the first electrical contact 106a connected to the heating element 105. FIG. 10 shows an exploded view of the electrode assemblies. Referring to FIG. 10, surrounding the central pins 130a, 130b are insulating sheaths 136a, 136b. The sheaths 136a, 136b are inserted into washers 138a, 138b. The washer 138a is in electrical communication with the outer electrode 107 on the proximal end 40p of the flexible circuit 40, while the washer 138b is in electrical communication with the second electrical contact 106b that is connected to the heating element 105. The sheaths 136a, 136b prevent the central pins 130a, 130b from contacting the washers 138a, 138b and shorting out the connections. The washers 138a, 138b are in electrical communication with the threads of the male threaded end 125 and the female threaded end 127, respectively, such that, when the first portion 15 and second portion 20 are joined, electrical communication is established between the first portion 15 and the second portion 20.

In order for this embodiment to be reusable, the electrical storage device 25 is rechargeable. In a preferred embodiment, the electrical storage device is a rechargeable 3.7V lithium-ion battery. In order to charge the electrical storage device 25, a variety of charging options exist, including charging cables and inductive charging. In a preferred embodiment, the electrical storage device is charged by inserted the first portion 15 into a charging case. The charging case contains a charging receptacle that features a reversible joint complementary to that of the first portion. The case is connected via cable to a power source. In one embodiment, the case is charged using a USB cable that can be plugged into a wall adapter. In another embodiment, the USB cable is plugged into a computer port.

Besides the reversible joint between the first portion 15 and the second portion 20 and the recharging capability, operation of the reusable embodiment is similar to the disposable embodiment. One benefit of the reusable embodiment is that the second portion 20, or cartomizer, is replaceable, so the user can change vaping liquids.

Dosage Control Embodiment

In another embodiment of the presently invented electronic cigarette 10, the dose of vaping liquid is controlled by the microprocessor, such that a user-programmable dose of vaping liquid is administered in each draw.

In this second embodiment, the electronic cigarette 10 contains many similar features as in the previous embodiment, including an electrical storage device 225, a microprocessor 230, an optional light or sensor 232, a vaporizer 234, a liquid reservoir 245, and a mouthpiece 50.

As in the previous embodiment and as shown in FIG. 11, the vaporizer 234 is contained in a cap 255. The cap 255 has an intermediate partition 260 that defines a first aperture 265. Extending from a first surface 260a of the partition 260 is a perimeter wall 270, having tall regions 275 and short regions 280. Extending from a second surface 260b of the partition 260 is a plug 281 that allows the cap 255 to be inserted into the liquid reservoir 245. The plug 281 is defined by a ring wall that is indented from the periphery of the second surface 260b. When the cap 255 is inserted into the liquid reservoir 245, the perimeter wall 270 preferably creates a smooth and continuous surface with the exterior of the liquid reservoir 245. Protruding from the medially facing surface of the perimeter wall 270 are ridges 285. The ridges 285 support a disc 287, containing electrical contacts 289a, 289b. The combination of the disc 287 and the short regions 280 of perimeter wall 270 define windows 292 in the cap 255. Disposed between and in electrical communication with the electrical contacts 289a, 298b is a heating element 290. The heating element 290 can be selected from a variety of suitable heating element types, including coils, thin films, and thick films. The heating element material is preferably selected from the heating element materials mentioned in the previous embodiments.

The dosage control embodiment operates in one of two ways. The first dosage control embodiment uses a heat pump to dispense vaping liquid from the reservoir. The second dosage control embodiment uses a diaphragm pump to dispense vaping liquid. Both embodiments use the same cap 255 discussed above; however, the components formed or inserted into the cap will vary.

Figure 14:
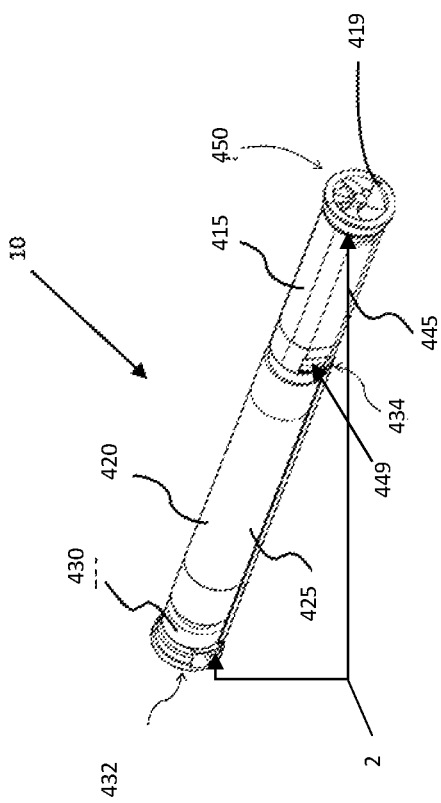
FIG. 14 depicts a perspective view of the dosage control embodiment.

In the diaphragm pump embodiment shown in FIG. 14, illustrated is a housing 2 and a first and second portion 415, 420 wherein the second portion 420 has a microprocessor 430 and a sensor 432, for detecting the airflow and communicating to the first portion 415. Also housed in the second portion 420 is the electrical storage device 225. The first portion 415 is provided with a vaporizer 234 including a heating element 449 and a liquid reservoir 445, which when activated produces vaporized product which is then consumed by a user via the mouthpiece 450 at the vortex outlet 419.

In the heat pump embodiment depicted in FIG. 12, the first surface 260a of the partition is overlaid with a substrate 295. A film 300 is placed over or deposited on the substrate 295. The film 300 is a second heating element and the materials for the film can be selected from the same materials as the heating element 290. The substrate 295 is preferably a silicon wafer with tracers embedded in it to carry current from the battery to the film 300. Formed through the thickness of the film 300 and substrate 295 is a second aperture 305 that lies in registration with the first aperture 265 in the intermediate partition 260. An inverted cup 310, having sidewalls 315 and a flat superior end 320, is placed over the film 300. The sidewalls 315 and flat superior end 320 define a heating region 325. The flat superior end 320 features a nozzle 330 having a depending capillary channel 331 that creates a fluid passageway from the heating region 325 (and thus, the liquid reservoir 245 by way of the first and second apertures 265, 305) and the exterior of the inverted cup 310.

When the user draws on the electronic cigarette 10, the microprocessor directs current to the heating element 290 and the film 300. The heat from film 300 causes a vapor bubble 332 to form in the capillary channel 331. As the vaping liquid continues to be heated, the vapor bubble 332 will pop, which ejects vaping fluid out of the nozzle 330 and onto the heating element 290 where it is vaporized. The vaporized liquid then exits from the vaporizer 234 through the windows 292. In the embodiment shown in FIG. 12, the cap 255 has a single aperture 265, heating region 325, and a single nozzle 330 with a single capillary channel 331, but the cap 255 could contain a plurality of heat pumps defined by those elements. Preferably, the cap 255 contains five or six heat pumps; although, more or less heat pumps could be included.

The heating region 325 is replenished with vaping liquid after the vapor bubble 332 bursts. Upon bursting, a vacuum is left behind in the region formerly occupied by the vapor bubble. The difference in pressure causes vaping liquid to flow into the heater region 325 so that a new vapor bubble 332 can form.

The film 300 is not heated to the same temperature as the heating element 290. Generally, the film 300 is heated to a maximum temperature of approximately 150° C. The heating element 290 will be heated to a maximum temperature of 300° C.

In the diaphragm pump embodiment shown in FIGS. 13A-B, the inverted cup 310 is placed over the substrate 295, creating a primer region 334. Embedded in the substrate 295 is a region defining a diaphragm 335. A piezoelectric transducer 340 is placed over the diaphragm 335. When current is supplied to the piezoelectric transducer 340, the piezoelectric transducer 340 will reversibly deform, causing the diaphragm 335 to deflect inwardly and outwardly. When the diaphragm 335 deflects inwardly as shown in FIG. 13A, the volume of the primer region 334 is decreased, which causes vaping liquid to be forced into the capillary channel 331 and ejected out of the nozzle 330 onto the heating element 290. When the diaphragm 335 deflects outwardly as shown in FIG. 13B, it draws more vaping liquid into the primer region 334. As in previous embodiments, when the vaping liquid contacts the heating element 290, it vaporizes and exits the vaporizer through the windows 292. Like in the heat pump embodiment, the diaphragm embodiment can contain a multitude of diaphragm pumps within the cap 255. Preferably, the cap 255 will contain 5 or 6 diaphragm pumps; although, more or less pumps can be included.

In both the heat and diaphragm pump embodiments, the vapor travels outside the reservoir 245 to the mouthpiece 50. As in the previous embodiments, the mouthpiece can contain a diffuser and a vortex outlet 119 as described in the previous embodiment.

In the dosage control embodiment, the microprocessor 230 performs many of the same functions as the microprocessor 30 of the previous embodiment, including, controlling the light 232, processing data from the sensor, and controlling current to the vaporizer 234. In this embodiment, though, the microprocessor 230 uses pulse width modulation to deliver pulses of current to the film 300 and the piezoelectric transducer 340 and to the heating element 290. Using pulsed current provides better temperature control of the film 300 and heating element 290 and allows finer tuning of the dosing of the piezoelectric transducer 340. The microprocessor 230 also runs on a timer, as in the previous embodiments, but, besides controlling current to the heating element 290, the timer also controls the amount of vaping fluid delivered by the heat or diaphragm pump and the maximum draw length (as selected by the user). Additionally, in some embodiments, the microprocessor 230 can communicate with outside equipment, such as applications or computers.

In the dosage control embodiment, the dosage of liquid delivered can be strictly controlled by the microprocessor 230 because the amount of liquid delivered can be precisely tuned using the heat or diaphragm pump. In this way, the user can set the dosage for each pump and the maximum dosage for a given period of time. The dosage can be set in a variety of suitable ways, including dials or buttons on the exterior of the electronic cigarette 10. If dials are used, the user would rotate or swivel a component of the electronic cigarette to select the dose from a continuous range of doses. If buttons are used, then the user would depress the button associated with the preselected dosage amounts. In a preferred embodiment, the dose is controlled wirelessly using, for instance, an application in communication with the electronic cigarette over Bluetooth or Wi-Fi.

This embodiment has particular applicability for those who use electronic cigarettes as a means to quit smoking and reduce their nicotine dependency. The electronic cigarette 10 provides a way to gradually taper the dose of nicotine, not only in each draw but also the daily amount.

Other embodiments of the invented electronic vaporization inhaler are easily envisioned, including medicinal delivery devices and atomizers.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

An exclusive right or privilege is claimed in the invention as defined in the following set of claims:

1. An electronic vaporizing inhaler, said electronic vaporizing inhaler comprising:
a housing having a first end comprising a liquid reservoir, a vaporizer, a heating element and a mouthpiece, and a second end configured to contain an electronic storage device, a sensor, and a microprocessor;
wherein the sensor is in electrical communication with the microprocessor and is configured to detect a change in pressure and to connect or disconnect the electrical communication which activates or deactivates the microprocessor,
wherein the microprocessor is in electrical communication with the electronic storage device and the sensor, and when activated by the sensor, the microprocessor is configured to direct current from the electrical storage device to the heating element in the vaporizer and to a plurality of piezoelectric transducers;
wherein the liquid reservoir is adapted to receive a vaping liquid and wherein the reservoir is in fluid communication with a primer region and a substrate comprising a plurality of diaphragm pumps;
wherein the vaporizer comprises:
the primer region, comprising:
an inferior end having a plurality of apertures providing fluid communication between the heating element and the liquid reservoir;
the substrate embedded with the plurality of diaphragm pumps, each diaphragm pump comprising a diaphragm and one of the plurality of piezoelectric transducers placed over the diaphragm, wherein each diaphragm flexes inwardly and outwardly in response to its corresponding piezoelectric transducer each in electrical communication with the microprocessor; and
a superior end having a plurality of nozzles, wherein each nozzle ejects the vaping liquid when its corresponding diaphragm flexes inwardly; and
wherein the heating element is proximal to the nozzles and in fluid communication with the reservoir and the vaping liquid, and in electrical communication with the electrical storage device such that when the microprocessor directs electrical current from the electrical storage device to the heating element and to the piezoelectric transducers, the piezoelectric transducers cause the diaphragms to flex causing the vaping liquid to be ejected from the nozzles such that the heating element vaporizes the liquid to vapor which a user can inhale from the mouthpiece at the first end of the housing; and wherein the mouthpiece is proximal to the vaporizer and at the housing first end such that a user of the electronic vaporizing inhaler can inhale vapor produced by the vaporization of the liquid by the vaporizer.

2. The electronic vaporizing inhaler of claim 1, wherein the microprocessor is configured to and send pulses of electrical current to the heating element and to the piezoelectric transducer.

3. The electronic vaporizing inhaler of claim 1, wherein the sensor is a digital pressure sensor.

4. The electronic vaporizing inhaler of claim 1, wherein the microprocessor is configured to receive input from the user concerning the dosage of vaping liquid per draw.

5. The electronic vaporizing inhaler of claim 1, wherein the primer region has 5 or 6 diaphragm pumps.

6. The electronic vaporizing inhaler of claim 1, further comprising a timer in electrical communication with the microprocessor and wherein the timer is activated when the microprocessor is activated by the sensor.

7. The electric vaporizing inhaler of claim 6, wherein the timer is configured to signal the microprocessor to disconnect the electrical communication between the electrical storage device and the heating element and the piezoelectric transducer at a preprogrammed time.

8. The electric vaporizing inhaler of claim 1, further comprising a light, wherein the microprocessor is also configured to be in electronic communication with the light and upon activation by the sensor, the microprocessor can turn on the light and control the intensity and duration of the light.

9. The electronic vaporizing inhaler of claim 1, wherein the electrical storage device is a lithium-ion or lithium-polymer battery.

10. The electronic vaporizing inhaler of claim 1, wherein the heating element is of a type selected from the group consisting of coils, thin films, thick films, and combinations thereof.

* * * * *